United States Patent
Atkinson

(10) Patent No.: US 11,755,661 B2
(45) Date of Patent: Sep. 12, 2023

(54) TEXT ENTRY ASSISTANCE AND CONVERSION TO STRUCTURED MEDICAL DATA

(71) Applicant: Roche Molecular Systems, Inc., Pleasanton, CA (US)

(72) Inventor: Craig Atkinson, Frenchs Forest (AU)

(73) Assignee: Roche Molecular Systems, Inc., Pleasanton, CA (US)

( * ) Notice: Subject to any disclaimer, the term of this patent is extended or adjusted under 35 U.S.C. 154(b) by 148 days.

(21) Appl. No.: 16/836,467

(22) Filed: Mar. 31, 2020

(65) Prior Publication Data

US 2021/0303630 A1    Sep. 30, 2021

(51) Int. Cl.
| | | |
|---|---|---|
| G06F 17/00 | (2019.01) | |
| G06F 7/00 | (2006.01) | |
| G06F 16/907 | (2019.01) | |
| G16H 10/60 | (2018.01) | |
| G06F 16/903 | (2019.01) | |
| G06F 16/9038 | (2019.01) | |

(Continued)

(52) U.S. Cl.
CPC .......... *G06F 16/907* (2019.01); *G06F 3/0482* (2013.01); *G06F 16/9024* (2019.01); *G06F 16/9038* (2019.01); *G06F 16/90335* (2019.01); *G06F 40/284* (2020.01); *G16H 10/60* (2018.01)

(58) Field of Classification Search
CPC ............. G06F 16/907; G06F 16/90335; G06F 16/9038; G06F 16/9024; G06F 40/284; G06F 3/0482; G16H 10/60
USPC ........................................................ 707/705
See application file for complete search history.

(56) References Cited

U.S. PATENT DOCUMENTS 5,267,155 A * 11/1993 Buchanan ............. G06F 40/174
715/210
6,813,603 B1 * 11/2004 Groner .................. G06F 40/174
704/235

(Continued)

FOREIGN PATENT DOCUMENTS

| WO | 2014/000267 A1 | 1/2014 |
| WO | 2014/134093 A1 | 9/2014 |
| WO | 2017/033084 A1 | 3/2017 |

OTHER PUBLICATIONS

International Search Report and Written Opinion in PCT/US2021/025130 dated Jul. 7, 2021; 12 pages.

*Primary Examiner* — Pavan Mamillapalli
(74) *Attorney, Agent, or Firm* — Kilpatrick Townsend and Stockton LLP

(57) ABSTRACT

A computer-implemented method is provided. The method comprises: receiving, from a text field of a user interface, input text strings containing medical data; identifying, based on language semantics and grammatical structure, a keyword and one or more data values from the input text strings; providing the keyword as an input to a query of a medical data category database to obtain one or more categories associated with the keyword, the one or more categories including a first category; retrieving, from a template database, a first template associated with the first category, the first template including one or more fixed blocks and one or more variable blocks; inserting a data value corresponding to the keyword into a variable block of the first template to generate a replacement text string; and displaying the replacement text string in place of the input text strings in the text field.

19 Claims, 13 Drawing Sheets

(51) Int. Cl.
*G06F 16/901* (2019.01)
*G06F 40/284* (2020.01)
*G06F 3/0482* (2013.01)

(56) References Cited

U.S. PATENT DOCUMENTS

| | | | | |
|---|---|---|---|---|
| 8,805,703 | B2 * | 8/2014 | Martin | A61B 5/0002 |
| | | | | 705/2 |
| 10,593,423 | B2 | 3/2020 | Baldwin et al. | |
| 2003/0220819 | A1 * | 11/2003 | Burstein | G06Q 10/10 |
| | | | | 705/3 |
| 2006/0041427 | A1 * | 2/2006 | Yegnanarayanan | G10L 15/26 |
| | | | | 704/235 |
| 2012/0173281 | A1 * | 7/2012 | DiLella | G16H 10/20 |
| | | | | 705/3 |
| 2016/0300573 | A1 * | 10/2016 | Carbune | G10L 17/22 |
| 2017/0046311 | A1 * | 2/2017 | Walker | G06F 40/289 |
| 2017/0308290 | A1 | 10/2017 | Patel | |
| 2019/0206522 | A1 * | 7/2019 | Baldwin | G06F 16/382 |
| 2019/0206524 | A1 * | 7/2019 | Baldwin | G06F 40/169 |

\* cited by examiner

| Medical data category | Keywords | Range of data values |
|---|---|---|
| Age | "age", "years of age", "age is", "is" | 1-150 |
| Weight | "weight", "weighs", "weight is", "is" | 50-1000 |
| Height | "height", "height is", "is" | Any number |
| Menopausal stage | "is", "meno", "peri", "post" | Menopausal, peri-menopausal, post-menopausal |
| Breast cancer stage | "has", "breast", "breast cancer" | 0, IA, IB, IIA, IIB, IIIA, IIIB, IIIC, IV |
| Type of Breast cancer | "has", "breast", "breast cancer" | ER+, HER2+, ER-, HER2-, Triple negative |
| Treatments | "undergo", "receive" | bilateral mastectomy, radiation therapy, Trastuzmab therapy, Paclitaxel therapy, no treatment |

502 — Jane Doe is a 64-year-old patient. She is post-menopausal. She has HER2+, HER-, stage IIa Breast cancer. She has undergone bilateral mastectomy and radiation therapy.

504 →

| Medical data category | Data values |
|---|---|
| Age | 64 |
| Menopause stage | Post-menopausal |
| Breast cancer stage | IIA |
| Type of Breast cancer | HER2+, ER- |
| Treatments | bilateral mastectomy, radiation therapy |

FIG. 5

TEXT ENTRY ASSISTANCE AND CONVERSION TO STRUCTURED MEDICAL DATA

BACKGROUND

Every day, healthcare providers create a tremendous amount of medical data across the globe. Analysis of medical data is critical to performing medical diagnosis, as well as determining and administering medical treatment, for the patients. The data can also provide detailed insights in healthcare delivery and quality of care provided by the healthcare provider.

Unfortunately, a large proportion of these medical data is entered into the system manually. The manual entry of medical data can be a very time-consuming, laborious, and error-prone process, which can degrade the reliability of the medical data in the system. Moreover, in many cases the medical data are entered as unstructured text strings. Unlike structured text strings, which may include text strings that are mapped to certain fields, codes, etc. that define the context and/or meaning of the mapped data, unstructured text strings may lack such a contextual mapping, which makes unstructured text strings difficult to access and analyze. All these can reduce the utility of the medical data.

BRIEF SUMMARY

Disclosed herein are techniques for facilitating entry of unstructured text strings into a text field of a user interface (e.g., a website, a portal, etc.), as well as converting the unstructured text strings into structured text strings.

In some examples, a system may receive, from a text field of a user interface, input text strings containing information of a patient entered by a user. The input text strings may include numerical values and phrases related to or indicative of a set of medical data of a patient, which comprises a medical data category as well as one or more data values. From the input text strings, the system may determine the medical data category and the one or more data values. The system may also generate replacement text strings representing a standardized expression of the medical data, and display the replacement text strings in place of the input text strings in the text field of the user interface. The replacement text strings can be stored as part of a medical record of the patient as unstructured medical data.

In some examples, the system may determine the replacement text strings by mapping words included in the input text strings to a medical data category table. The medical data category table may store a plurality of medical data categories, with each medical category being associated with one or more keywords. Responsive to extracting one or more of those keywords in the input text strings, the system can identify the medical data category associated with those keywords from the medical data category table. The system may also extract the one or more data values for that medical data category. The system can then construct the replacement text strings which represents a standardized expression of the medical data based on the medical data category and the one or more data values.

In some examples, the system may determine the replacement text strings based on additional inputs from the user. For example, the system can determine one or more candidate expressions based on mapping the words of the input text strings to the medical data category table, and display the one or more candidate expressions in the user interface for selection. Upon receiving a selection from the user, the system can enter the selected candidate expression into the text field on behalf of the user. Various techniques can be employed to determine the one or more candidate expressions. In one example, the system can determine a degree of similarity between the input text strings and the one or more keywords associated with each medical data category in the medical data category table, and rank the medical data categories based on the degree of similarities. The system can then generate the one or more candidate expressions for the top-ranked medical data categories and display the candidate expressions for selection. In another example, the system can also determine a likelihood of each candidate expression reflecting the intent of the user, and rank the candidate expression according to the likelihood. In yet another example, the system can also maintain a frequency count of selection of the medical data categories by the user, and rank the candidate expressions based on the frequency counts.

In some examples, the system can also predict a next set of medical data the user is likely to enter into the text field, generate expression representing the predicted medical data, and enter the expression into the text field on behalf of the user. The prediction can be based on, for example, prior sequences of medical data entered into the text field by the user or by a group of users. The sequence of medical data include a sequence of medical data categories of the medical data category table. The system can predict, based on the medical data category of the medical data most recently entered into the text field, one or more medical data categories of the next set of medical data. The system can generate one or more candidate expressions representing the predicted medical data (comprising medical data categories and candidate data values), and display the expressions for selection. Upon receiving the selection, the system can then enter the selected candidate expression into the text field on behalf of the user.

In some examples, the system can also generate structured medical data for the patient. The structured medical data can be created by, for example, creating pairing between medical data categories and data values during the generation of replacement text strings and the prediction of medical data. As the system continues generating standardized expressions including the medical data and entering the expressions into the user interface, the system can create pairing of different medical data categories and different medical data as part of the structured medical data for the patient. The system can also store the expressions entered into the user interface as unstructured medical data for the patient. Both the structured and unstructured medical data can be stored as part of the medical record of the patient.

These and other examples of the present disclosure are described in detail below. For example, other examples are directed to systems, devices, and computer readable media associated with methods described herein.

A better understanding of the nature and advantages of examples of the present disclosure may be gained with reference to the following detailed description and the accompanying drawings.

BRIEF DESCRIPTION OF THE DRAWINGS

The detailed description is set forth with reference to the accompanying figures.

FIG. 3A and FIG. 3B illustrate internal components and operations of the text-entry assist system of FIG. 2, according to certain aspects of the present disclosure.

FIG. 5 illustrates example medical records created by the text-entry assist system of FIG. 2, according to certain aspects of the present disclosure.

DETAILED DESCRIPTION

Figure 1A:
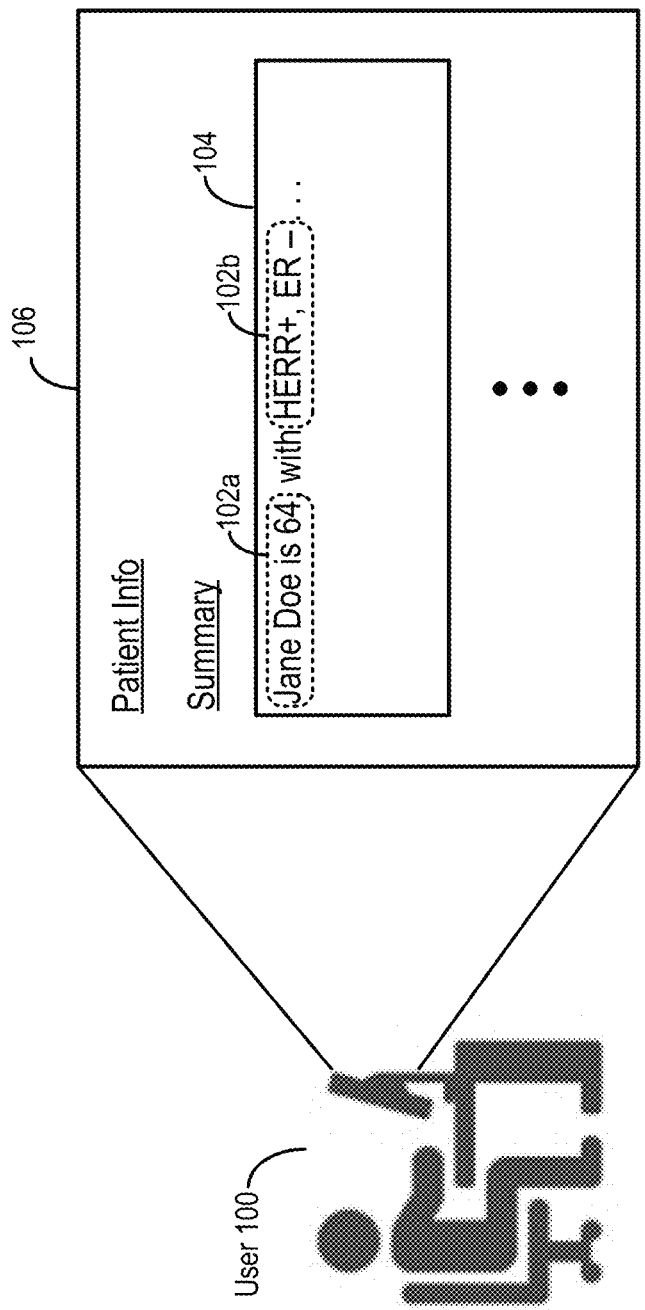
FIG. 1A and FIG. 1B illustrate example methods of creating medical record of a patient.

Disclosed herein are techniques for facilitating entering of unstructured text strings into a text field of a user interface (e.g., a website, a portal, etc.), as well as converting the unstructured text into structured text strings. The user interface can be part of a medical application that accepts text strings representing unstructured medical data input by a user (e.g., a clinician, a medical staff member, a data entry clerk, etc.), that stores the text strings, and that provides the medical data represented by the text strings for further processing, presentation, etc. Examples of the unstructured medical data can include, for example, pathological reports, doctor's notes, etc. The techniques can be implemented by a text-entry assist system that can be part of the user interface, or can be external to the user interface.

In some examples, a system may receive, from the text field of the user interface, one or more input text strings containing information of a patient from a user. The input text strings may include numerical values and phrases related to or indicative of a set of medical data of a patient. Each entry of the medical data can include a medical data category as well as one or more data values. For example, the medical data may include an age, a weight, a diagnosis result, treatment history, etc. The input text strings may include incomplete or a non-standardized expression of the patient's information. From the input text strings, the system may generate replacement text strings representing a standardized expression of the set of medical data, and display the replacement text strings in place of the input text strings in the text field of the user interface. The replacement text strings can be stored as part of a medical record of the patient.

The system may determine the replacement text strings by mapping words included in the input text strings to a medical data category table. The medical data category table may store a plurality of medical data categories such as, age, weight, diagnosis, etc., with each medical category being associated with one or more keywords. The one or more keywords may include complete or incomplete phrases included in prior expressions provided by the user (or by other users) to represent the associated medical data category. As an illustrative example, the user may have provided keywords such as "is", "age is", "years of age", etc., in an expression to represent the age of a patient. Responsive to extracting one or more of those keywords in the input text strings, the system can identify the medical data category associated with those keywords from the medical data category table (e.g., patient's age). The system may also extract one or more data values for that medical data category (e.g., a number representing the patient's age). The system can then construct the replacement text strings that represent a standardized expression of the medical data comprising the medical data category and the one or more data values. The standardized expression can be generated such that different expressions of the same category of medical data (e.g., patient's age) can be converted to the same form of expression for that medical data category. For example, expressions such as "Jane Doe is 64", "Jane Doe's age is 64", "Jane Doe is 64 years of age," etc., can all be converted to the standardized expression "Jane Doe is a 64-year-old patient."

The system may determine the replacement text strings based on additional inputs from the user. For example, the system can determine one or more candidate expressions based on mapping the keywords of the input text strings to the medical data category table. The system can also display the one or more candidate expressions in the user interface for selection. Upon receiving a selection from the user, the system can determine the selected candidate expression as the replacement text strings. Various techniques can be employed to determine the one or more candidate expressions. In one example, the system can determine a degree of similarity (e.g., based on cosine distance, Euclidean distance, etc.) between the input text strings and the one or more keywords associated with each medical data category in the medical data category table, and can rank the medical data categories based on the degree of similarities. The system can then generate the one or more candidate expressions for the top-ranked medical data categories and display the candidate expressions for selection. In another example, the system can also determine a likelihood of a medical data category being correctly associated with the one or more data values for each candidate expression, and rank the candidate expressions accordingly. For example, while a number "64" can mean age, weight (e.g., in pounds (lbs)), and height (e.g., in inches), the system may determine that the number most likely refers to an age rather a weight or a height. In yet another example, the system can also maintain a frequency count of selection of the medical data categories by the user, and rank the candidate expressions based on the frequency counts.

In some examples, the system can predict a next set of medical data the user is likely to enter into the text field. The system can generate an expression representing the predicted medical data, and enter the expression into the text field on behalf of the user. The prediction can be based on, for example, prior sequences of medical data entered into the text field by the user or by a group of users. A sequence of medical data can include a sequence of medical data categories of the medical data category table. The system can predict, based on the medical data category of the medical data most recently entered into the text field, one or more medical data categories of the next set of medical data. The system can generate one or more candidate expressions representing the predicted medical data (comprising medical data categories and candidate data values), and display the expressions for selection. Upon receiving the selection, the system can then enter the selected candidate expression into the text field on behalf of the user.

In some examples, the system can generate structured medical data for the patient. For example, upon determining that an input text string "Jane Doe is 64" represents an expression of age of the patient, the system can create structured medical data such that the age of the patient is associated with the value 64. The structured medical data can be created by, for example, populating the medical data category table to associate the age category with the value 64. As the system continues generating standardized expressions including the medical data (e.g., based on detecting additional text strings entered by the user, based on predicting the text strings to be entered by the user, etc.), the system can create pairing of different medical data categories and different medical data as part of the structured medical data for the patient. The structured medical data can also be stored as part of the medical record of the patient.

With the disclosed techniques, a system having a user interface can assist the user in entering the medical data of a patient as part of the medical record by determining what the user intends and replacing the text strings entered by the user with standardized expressions of the medical data. Such arrangements not only can reduce the time and effort spent by the user in completing the entry of the medical data, but also ensure that the expression, being standardized, can represent the medical data unambiguously and provide a context to facilitate understanding of the expression. The system can also automatically generate structured medical data for the patient based on identifying a standardized expression and mapping the medical data, which can be extracted from the text strings entered by the user or can be determined based on a user selection, to the appropriate medical data category. The structured medical data can be added to a medical record of the patient. All these can improve the efficiency in generating the medical record as well as the utility of the medical record. With the improvements in the overall speed of data flow and in the correctness and completeness of patient data, wider and faster access of high-quality patient data can be provided for clinical and research purposes, which can facilitate the development in treatments and medical technologies, as well as the improvement of the quality of care provided to the patients.

I. Generating a Medical Record

Figure 1B:
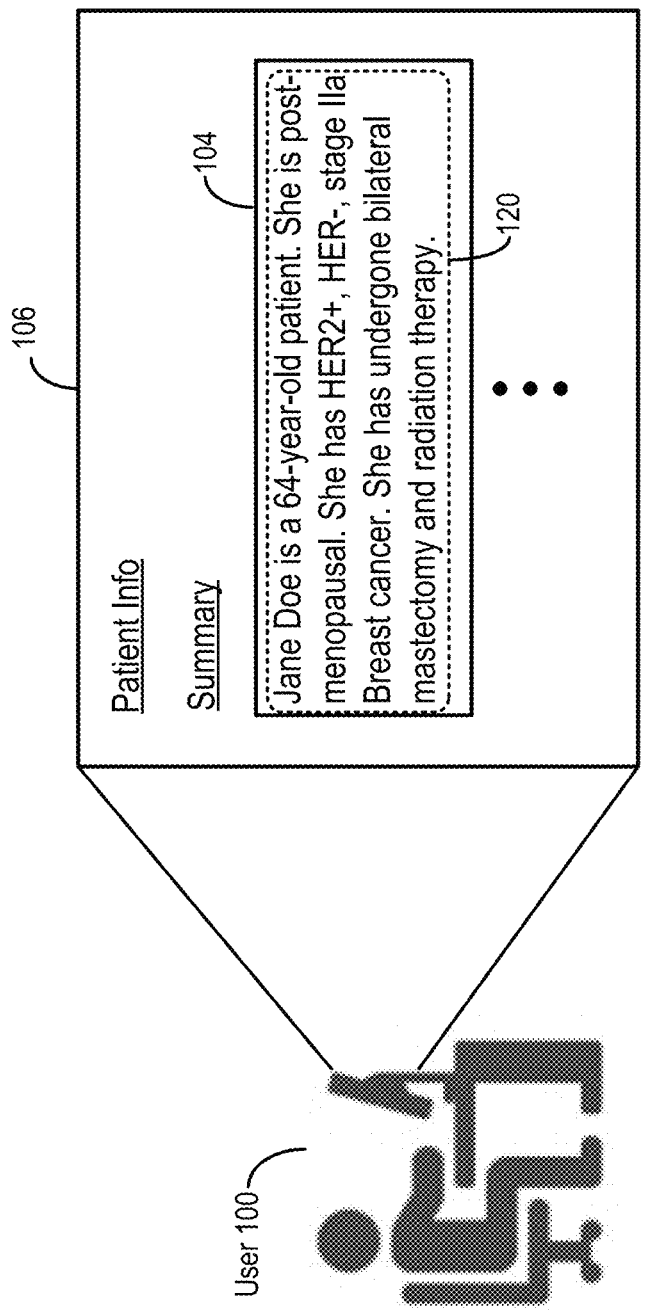

FIG. 1A and FIG. 1B illustrate methods of creating medical record of a patient based on entering text strings that may be improved by the present disclosure. As shown in FIG. 1A, a user 100, such as a clinician, a medical staff member, a data entry clerk, etc., can manually enter text strings, including text strings 102a and 102b, into a text field 104 of a medical application portal 106. The medical application can then store text strings 102a and 102b as part of a medical record for a patient. The text strings can be part of unstructured medical data including, for example, a pathological report, doctor's notes, a summary of patient's information, etc., to be entered into different fields of medical application portal 106. The text strings entered into the field can be stored in the medical record for the patient. The text strings can also be parsed by a human (e.g., a clinician) to obtain structured medical data for the patient. In structured medical data, each data value can be explicitly linked with a medical data category to provide a context for interpreting the data value.

The manual entry of text strings can be a very time-consuming, laborious, and error-prone process. Moreover, different people may use different expressions to represent the same information, which can lead to ambiguity and incorrect interpretation of the text strings, especially when the text strings are interpreted by a machine. For example, referring to FIG. 1A, text strings 102a, which includes the phrase "Jane Doe is 64," might be interpreted by a machine to mean any one of "Jane Doe's age is 64", "Jane Doe's weight is 64 lbs.", "Jane Doe's height is 64 inches", etc.

Moreover, some of the text strings may include typos, which can be determined only if the context of the text strings is understood. For example, the user may have intended to type "HER2+, ER−" in text strings 102b as opposed to "HERR+, ER−", where "HER2+" can refer to Human epidermal Growth Factor Receptor 2 (HER2) positive and "ER−" can refer to Estrogen negative, both of which refer to a specific type of breast cancer. Without understanding that the patient has breast cancer, it may be impossible to determine the actual meaning of "HERR+" of text strings 102b and detect that there is a typo in the text strings entered by user 100. In addition, there can be other medical data that user 100 inadvertently skipped entering, such as a menopausal stage of the patient, the treatment the patient has received, etc. Moreover, the meaning of the entered text strings can also be interpreted different by different people, if the entered text strings do not include standardized expressions.

FIG. 1B illustrates another example of text strings 120 that include a more complete and clear representation of the medical data of the patient. As shown in FIG. 1B, text strings 120 include expressions that clearly convey that the number "64" refers to the age of the patient. Text strings 120 also states that the patient is post-menopausal, that the patient has HER2+ HER− breast cancer, and the breast cancer is at stage IIa. The text strings "HER2+" and "HER−" can be standardized expressions. Text strings 120 also lists the treatments the patient has received.

While text strings 120 shown in FIG. 1B can provide a more complete and clear representation of the medical data of the patient, various limitations of the manual entry process of text strings 120 still exist and can degrade the reliability of the medical data. For example, entering text strings 120 to include the full set of medical data can be time-consuming, laborious, and error-prone, especially for a large number of patients. In addition, given that text strings 120 represent unstructured medical data, there may still be a need to convert text strings 120 to structured medical data, in which each medical category is clearly linked to a piece of medical data, for further analysis and presentation. Having a separate system/person scanning through text strings 120 entered for each patient to extract medical data and converting them into a structured format for each patient may also be time-consuming, laborious, and error-prone.

II. Text-Entry Assist System

Disclosed herein are techniques for facilitating entering of unstructured text strings into a text field of a user interface (e.g., a website, a portal, etc.), as well as converting the unstructured text into structured text strings. In some examples, a system may receive, from the text field of the user interface, one or more input text strings containing information of a patient from a user. From the input text strings, the system may generate replacement text strings representing a standardized expression of the set of medical data, and display the replacement text strings in place of the input text strings in the text field of the user interface. The system may determine the replacement text strings by mapping words included in the input text strings to a medical data category table. The medical data category table may store a plurality of medical data categories, with each medical category being associated with one or more keywords. From the keywords in the input text strings, the system can identify the medical data category associated with those keywords from the medical data category table. The system can then construct the replacement text strings based on the medical data category.

A. System Overview

Figure 2:
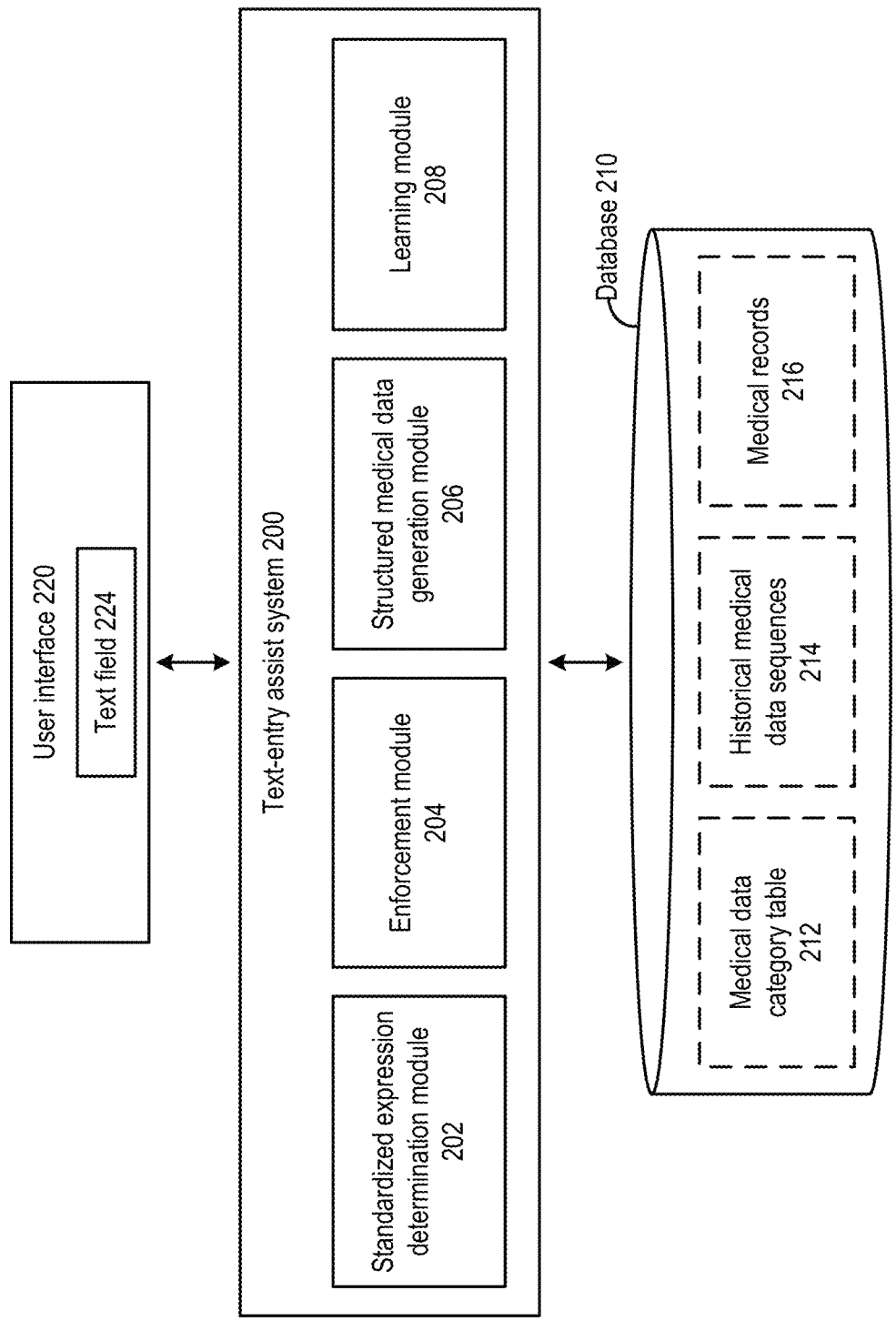
FIG. 2 illustrates an example text-entry assist system, according to certain aspects of the present disclosure.

FIG. 2 illustrates an example text-entry assist system 200 that can facilitate entry of unstructured text into a text field of a user interface (e.g., a website, a portal, etc.), as well as converting the unstructured text into structured text strings. As shown in FIG. 2, text-entry assist system 200 may include a standardized expression determination module 202, a structured medical data generation module 204, an enforcement module 206, and a learning module 208. Text-entry assist system 200 can be coupled to a database 210, which can store a medical data category table 212, historical medical data sequences 214, and medical records 216. In some examples, each of medical data category table 212, historical medical data sequences 214, and medical records 216 can be implemented as a database, so that database 210 includes multiple databases. Text-entry assist system 200 can be implemented as software codes and executed on a computer to perform the functions as to be described below.

As shown, text-entry system 200 is also coupled with an user interface 220, which includes a text field 224 to receive text strings that can represent unstructured medical data. User interface 220 can be part of a medical application that accepts text strings entered by a user (e.g., a clinician, a medical staff member, a data entry clerk, etc.) via text field 224, stores the text strings and provides the medical data represented by the text strings for further processing, presentation, etc. Examples of the unstructured medical data can include, for example, pathological report, doctor's notes, etc. In some examples, text-entry assist system 200 can be part of the medical application that provides user interface 220.

In some examples, text-entry assist system 200 may receive, from text field 224 of user interface 220, input text strings containing information of a patient entered by a user. The input text strings may include numerical values and phrases related to or indicative of a first medical data category (e.g., age, weight, diagnosis, treatment, etc.) as well as first medical data of that patient for the first medical data category (e.g., the patient's age, the diagnosis result of the patient, the treatment received by the patient, etc.). The input text strings may include incomplete or a non-standardized expression of the patient's information.

As to be described in details below, standardized expression determination module 202 can extract keywords from the input text strings, and search for those keywords in medical data category table 212. Medical data category table 212 may store a plurality of medical data categories, with each medical data category being associated with one or more keywords. Standardized expression determination module 202 can determine that the input text strings include a first medical data category based on, for example, matching the keywords extracted from the input text strings with the keywords associated with the first medical data category in medical data category table 212. Standardized expression determination module 202 can also extract one or more data values associated with the first medical data category from the input text strings, and generate replacement text strings representing a standardized expression of the first medical data category and the first medical data. Standardized expression determination module 202 can provide the replacement text strings to user interface 220 for displaying in text string field 224 in place of the input text strings. In some examples, standardized expression determination module 202 can provide a set of candidate replacement text strings in user interface 220 for selection, and display the selected candidate replacement text strings. Based on the selection by the user, the replacement text strings can also be stored as part of medical records 216.

In some cases, standardized expression determination module 202 may be unable to identify the keywords included in the input text strings in medical data category table 212. In some examples, learning module 208 can add the unidentified keywords to one of the existing medical data categories or create a new medical data category for the keywords. Enforcement module 204 may also cause user interface 220 to reject the input text strings based on, for example, not accepting the input text strings in text field 224 or not generating the replacement text strings, to force the user to include keywords stored in medical data category table 212 in the input text strings entered through text field 224.

In some examples, standardized expression determination module 202 can also predict text strings that are likely to be entered by the user subsequent to the input text strings. The prediction can be based on historical medical data sequences 214, which can include prior sequences of medical data entered into user interface 220 by the user or by a group of users. Based on the first medical data category included in the input text strings and from the prior sequences of medical data, the system can predict a next set of medical data likely to be entered by the user. Standardized expression determination module 202 can generate candidate prediction text strings representing the next set of medical data that includes a medical data category and candidate data values, and display the candidate prediction text strings in user interface 220 for selection. Upon receiving a selection from the user, standardized expression determination module 202 can add the selected text strings in text field 224 of user interface 220. Standardized expression determination module 202 can also update historical medical data sequences 214 to reflect the selection.

In addition, medical records 216 for the patients can also be updated based on the replacement text strings and/or prediction text strings generated for text field 224. For example, structured medical data generation module 206 can create pairings of the medical data categories and the data values and store the pairings in certain data structures (e.g., data tables) of medical records 216. Moreover, standardized expression determination module 202 can also store the replacement text strings and prediction text strings in medical records 216 as unstructured medical data for the patient.

B. Generation of Replacement Text Strings

Figure 3B:
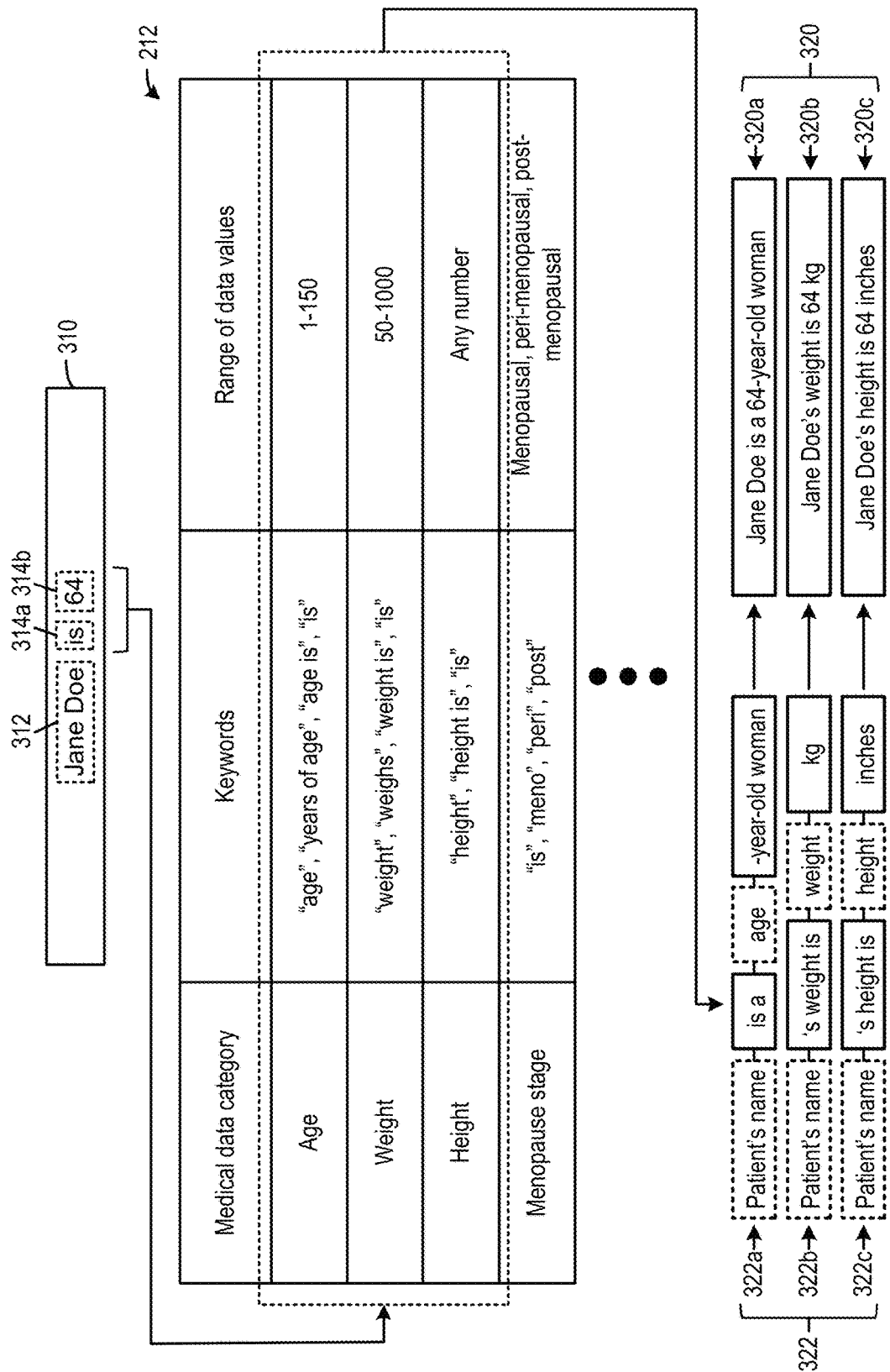

FIG. 3A and FIG. 3B illustrate an example of medical data category table 212 stored in database 210 and operations involving medical data category table 212 in the generation of replacement text strings. As shown in FIG. 3A, medical data category table 212 may store a plurality of medical data categories 302 specific for a patient having breast cancer, such as, age, weight, height, menopause stage, breast cancer stage, type of breast cancer, treatments, etc. In some examples, database 210 may store multiple medical data category tables, with each table specific for a type of illness (e.g., breast cancer, lung cancer, etc.). A medical data category table can be selected by the system based on a type of illness of the patient. For example, prior to entering text strings into text field 224, user interface 220 can prompt the user to select a type of illness of the patient. Based on the user's selection, text-entry assist system 200 can select a medical data category table for generation of replacement text strings.

Medical data category table 212 may also store keywords 304, with each medical data category being associated with one or more keywords. The keywords can be used by standardized expression determination module 202 to identify a medical data category included in input text strings received from the user via user interface 220. For example, as shown in FIG. 3A, the medical data category "age" can be associated with a set of keywords such as "age", "years of age", "age is", "is", etc. If the input text strings include at least one of those keywords, standardized expression determination module 202 can determine that the input text strings include the medical category "age". Standardized expression determination module 202 can determine a medical category within a pre-determined delay (e.g., 10 milliseconds) after it receives a first set of input text strings from which keywords can be identified (e.g., text strings 102a in FIG. 1A), and prior to receiving a subsequent set of input text strings from text field 224 (e.g., text strings 102b in FIG. 1A).

The keywords in medical data category table 212, as well as their association with the medical data categories, can be provided off-line by the user, by a manager of text-entry assist system 200 (e.g., based on analyzing the keywords used by a group of users to represent a medical data category), or based on an on-line learning process by learning module 208 as to be described below. In some examples, keywords 304 can include expressions/phrases in an non-English language (e.g., German, Spanish, etc.), which can be mapped to medical categories 302 and range of data values 306 represented in English.

In addition, medical data category table 212 may also store ranges of data values 306, with each medical data category being associated with a range of data values. In some examples, the range of data values associated with a particular medical data category can be used by standardized expression determination module 202 to extract medical data from the input text. For example, based on determining that the input text strings include the key phrases "age is", which indicates that the input text strings includes the medical data category "age", standardized expression determination module 202 can extract a numerical value between 1-150 from the input text strings. The numerical value can represent the age of the patient included in the input text strings. In some examples, instead of determining a single medical category, standardized expression determination module 202 can also determine a range of candidate medical categories. As to be described below, the range of medical data values and/or the range of candidate medical categories can be used to construct replacement text strings candidates, one of which can be selected by the user to enter into user interface 220 as replacement text strings.

FIG. 3B illustrates an example operation of generating replacement text strings by standardized expression determination module 202 based on medical data category table 212. As shown in FIG. 3B, standardized expression determination module 202 can receive input text strings 310 from text field 224 of user interface 220. In the example of FIG. 3B, input text strings 310 include the phrase "Jane Doe is 64". From input text strings 310, standardized expression determination module 202 can apply various techniques, such as natural language processing (NLP), and based on language semantics and grammatical structure, to extract various information from input text strings 310. For example, standardized expression determination module 202 can determine, based on a NLP model developed based on language semantics and grammatical structure and trained based on sequences of text strings, that text strings 310 include a subject (Jane Doe), a verb ("is"), and a noun ("64"), and divide text strings 310 into a text string 312 (Jane Doe), a text string 314a ("is"), and a text string 314b ("64").

Standardized expression determination module 202 may determine, based on text string 312 is a subject, that "Jane Doe" is most likely the patient's name. Moreover, based on identifying that text string 314b includes a numerical value, standardized expression determination module 202 may determine that text string 314b includes a medical data value for the patient. Standardized expression determination module 202 can then determine that text string 314a (or a portion of it) is potentially a keyword.

After extracting text string 314a, standardized expression determination module 202 can search for text string 314a in medical data category table 212 to determine whether text string 314a match any of the keywords associated with the medical data categories in medical data category table 212. In the example of FIG. 3B, standardized expression determination module 202 can determine that the text string 314a "is" matches the keyword associated with the medical data categories "age", "weight, and "height", and can determine that input text strings 310 likely intend to provide either the age, weight, or height of the patient Jane Doe, and the number 64 can refer to the age, weight, or height of Jane Doe.

Based on the determination that input text strings 310 likely intend to provide either the age, weight, or height of the patient, standardized expression determination module 202 can generate a set of candidate replacement text strings 320 based on a set of pre-determined templates 322, each including a standardized expression to represent the age, weight, or height of the patient. Each template can be pre-determined for a specific medical data category. For example, template 322a is for age, template 322b is for weight, whereas template 322c is for height. Each of templates 322 can include one or more fixed blocks and one or more variable blocks. The fixed blocks can include pre-determined text strings of a standardized expression, such as "is a", "year-old woman", etc. The variable blocks can be filled in with the identified medical data category other information extracted from the input text strings. Pre-determined templates 322 can be in the English language and can be obtained from a template database, which can be part of database 210. The templates stored in the template database can be associated with the medical data category table(s). In some examples, the templates can include gender information based on the type of illness (e.g., breast cancer) associated with medical data category table 212.

Standardized expression determination module 202 can then generate candidate replacement text strings 320a, 320b, and 320c by filling in the variable blocks of the respective templates with the patient's names and the medical data value extracted from text strings 314b. In a case where keywords 304 contain expressions/phrases in a non-English language, standardized expression determination module 202 can generate English candidate replacement text strings 320 to not only standardize the text strings but also translate non-English phrases/expressions into English.

The candidate replacement text strings 320 can be provided to user interface 220 for display and for selection by the user. One of the candidate replacement text strings 320, upon selection, can then be entered into text field 224 to replace input text strings 310. In some examples where a single candidate replacement text strings 320 is generated due to, for example, text strings 314a matching the keywords of only one medical data category, standardized expression determination module 202 can automatically replace input text strings 310 with the single candidate replacement text strings 320 in text field 224 without receiving a selection from the user.

With the arrangements of FIG. 3B, different expressions of the same category of medical data (e.g., patient's age) can be converted to the same form of expression for that medical data category. For example, expressions such as "Jane Doe is 64", "Jane Doe's age is 64", "Jane Doe is 64 years of age," etc., can all be converted to the standardized expression "Jane Doe is a 64-year-old patient."

In some examples, standardized expression determination module 202 can rank the candidate replacement text strings 320, and change the display of the candidate text strings in user interface 220 according to the ranking to assist the user in selecting the replacement text strings. In one example, standardized expression determination module 202 can rank the candidate replacement text strings 320 based on a likelihood that the medical data value, extracted from text strings 314b, is associated with a particular medical data category. For example, referring the numerical value 64, while such a numerical value can refer to an age, to a weight (e.g., 64 lbs), or to a height (e.g., 64 inches), standardized expression determination module 202 can determine that the numerical value of 64 more likely indicates an age, since a weight of 64 lbs is far below an average weight of an adult, while the height of a human being is seldom expressed in inches.

Various techniques can be implemented to assist standardized expression determination module 202 in determining the likelihood of a numerical value being associated with a particular medical data category. For example, medical data category table 212 can include, for each medical data category involving a numerical value (e.g., a weight, an age, etc.), a probability distribution of the numerical values, and the same medical data category can have different probability distributions in different medical data category table for different types of illnesses. Moreover, the probability distribution of a numerical value can be a function of another numerical value. For example, medical category table 212 can store different probability distributions of a numerical value of weight for different ages. After standardized expression determination module 202 determines a numerical value of age (e.g., based on the probability distribution of age), determination module 202 can use the age to select a probability distribution of weight, and determine a set of the most likely numerical values of weight and the associated unit(s).

Based on determining the likelihoods of a numerical value being associated with different data categories, standardized expression determination module 202 can rank the candidate replacement text strings 320a (representing an age) first, followed by candidate replacement text strings 320b (representing a weight), and then followed by candidate replacement text strings 320c (representing a height), and display these candidate text strings in user interface 220 in an order (e.g., from closest to furthest to text field 224) according to the ranking.

As another example, standardized expression determination module 202 can also rank the candidate replacement text strings 320 based on a history of selection by the user for a particular keyword entered. If the history of selection indicates that after the user has entered the patient's name, followed by the word "is" and a number, the user has selected a candidate replacement text strings representing an age far more often than other candidate replacement text strings representing other medical data categories, standardized expression determination module 202 can determine that the text strings entered by the user is the user's preferred way of entering the age of a patient, and can rank the candidate replacement text strings representing an age the highest. The history of selection can be recorded based on, for example, counting the user's prior selection of a particular template (or a particular set of templates) for a particular medical category. In some examples, user interface 220 is accessible only after a user logs into a system, and standardized expression determination module 202 can determine the user who enters the input text strings and makes the selection, and track the user's history of selection, based on the login information (e.g., credentials, etc.) provided by the user.

C. Handling of Unidentified Keywords from the User

In some cases, text-entry assist system 200 may be unable to identify the keywords included in the input text strings in medical data category table 212. This can be due to, for example, the user (or a different user) using a new expression to represent a medical data category, a typo by the user, etc.

Text-entry assist system 200 can handle an unidentified keyword/phrase based on, for example, determining a degree of similarity between the unidentified keyword/phrase and each keywords stored in medical data category table 212. In one example, standardized expression determination module 202 can compute a degree of similarity between the unidentified keyword/phrase and each keywords stored in medical data category table 212 to determine the closest medical data categories, generate a set of candidate replacement text strings, and display them in user interface 220 for selection. The degree of similarity can be based on, for example, a cosine distance, a Euclidean distance, or any other suitable metrics, whereas the closest medical data categories can be determined based on, for example, the metrics of the degree of similarity for those categories exceeding a threshold. Learning module 208 can determine which candidate replacement text strings is selected by the user, identify the corresponding medical data category, and add the unidentified keyword/phrase to that medical data category medical data category table 212.

In a case where the metrics of the degree of similarity between the unidentified keyword/phrase and each keywords stored in medical data category table 212 are below the threshold, text-entry assist system 200 can handle the unidentified keyword/phrase in various ways. For example, standardized expression determination module 202 can still determine a medical data category of which the keyword is the closest to the unidentified keyword/phrase but the degree of similarity is below the threshold, and provide the candidate replacement text strings for the medical data category to the user for selection, which can be detected by learning module 208. Learning module 208 can also prompt the user to enter a new medical data category for the unidentified keyword/phrase, and store the new medical data category and the unidentified keyword/phrase into medical data category table 212.

As another example, enforcement module 204 may also cause user interface 220 to reject the input text strings including the unidentified keyword/phrase based on, for example, not accepting the input text strings in text field 224 or accepting the input text strings in text field 224 but not generating the replacement text strings to replace the input text strings. Enforcement module 204 can also provide the unidentified keyword/phrase to the manager of text-entry assist system 200, who can analyze the input text strings offline and determine whether and how to add the unidentified keyword/phrase into medical data category table 212.

D. Generation of Prediction Text Strings

In some examples, after receiving input text strings from the user via user interface 220 and replacing the text strings with a standardized expression of medical data as described above, standardized expression determination module 202 can predict a next set of medical data the user is likely to enter into user interface 220. The prediction can be based on historical medical data sequences 214, which can store information related to prior sequences of medical data entered into user interface 220. Based on the prediction, standardized expression determination module 202 can generate one or more candidate prediction text strings representing the predicted medical data, and display the candidate prediction text strings in user interface 220 for selection by the user. The selected candidate prediction text strings can then be entered into user interface 220 as the next set of medical data. Such arrangements can further reduce the effort and improve the efficiency and accuracy in entering the medical data into user interface 220.

Figure 4A:
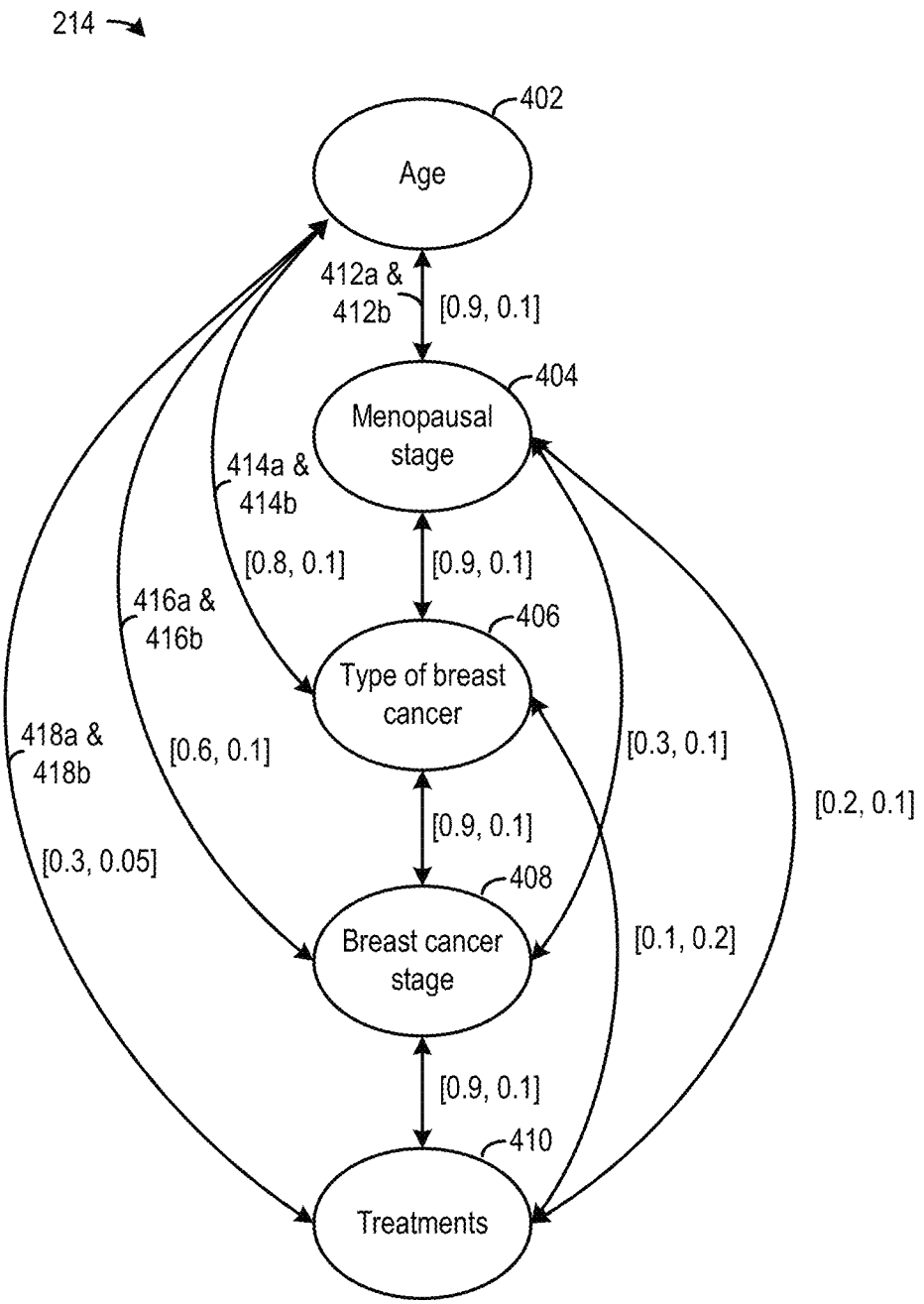
FIG. 4A and FIG. 4B illustrate examples of historical medical data sequences used in the operations of text-entry assist system of FIG. 2, according to certain aspects of the present disclosure.
Figure 4B:
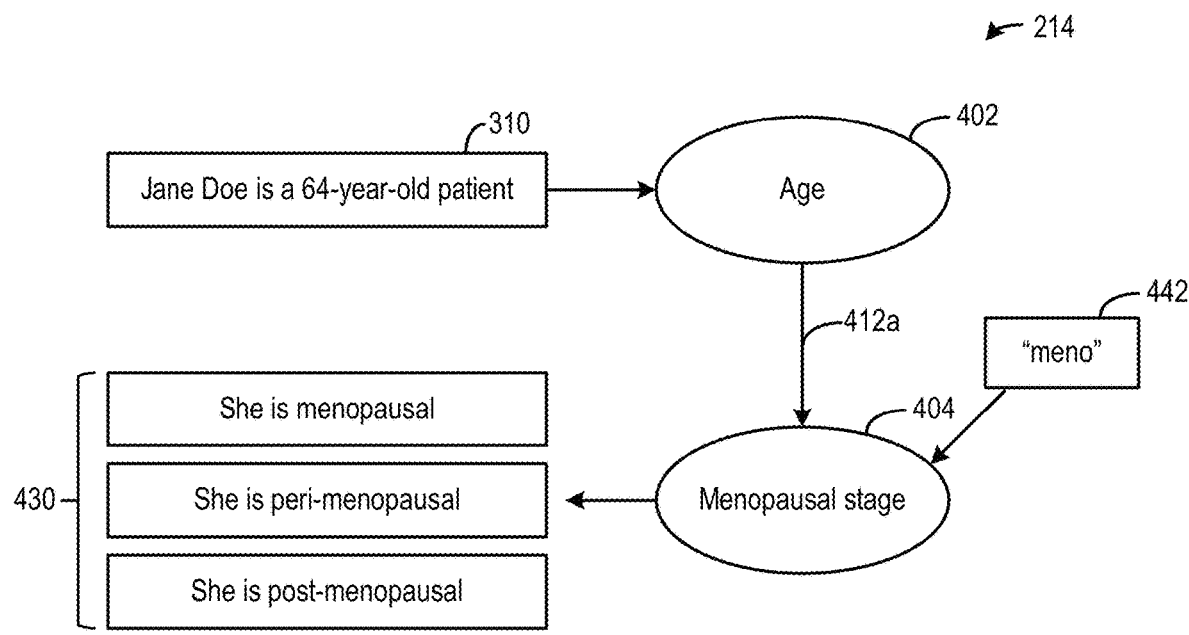

FIG. 4A and FIG. 4B illustrate an example of historical medical data sequences 214 stored in database 210, as well as operations involving historical medical data category sequences 214 in the generation of replacement text strings. FIG. 4A illustrates an example of historical medical data sequences 214. As shown in FIG. 4A, historical medical data sequences 214 can be in the form of a graph including a set of nodes connected by directional edges. Each node can represent a medical data category included in, for example, medical data category table 212. For example, node 402 represents the medical data category "age", node 404 represents the medical data category "menopause stage", node 406 represents the medical data category "type of breast cancer", node 408 represents the medical data category "breast cancer stage", whereas node 410 represents the medical data category "treatments". The graph can be stored in database 210 in various formats, such as linked list, table, etc., with each node being linked to a medical data category in medical data category table 212.

Each node in the graph of historical medical data category sequences 214 can be connected to another node via a pair of directional edges. Each pair directional edges can represent transitions between one medical data category to another medical category. For example, pair of edges 412a and 412b can represent, respectively, a transition from node 402 (age) to node 404 (menopausal stage), and vice versa. Pair of edges 414a and 414b can represent, respectively, a transition from node 402 (age) to node 406 (type of breast cancer), and vice versa. Moreover, pair of edges 416a and 416b can represent, respectively, a transition from node 402 (age) to node 408 (breast cancer stage), and vice versa. Further, pair of edges 418a and 418b can represent, a transition from node 402 (age) to node 408 (treatments), and vice versa.

A transition from one node to another node can indicate a sequential relationship between the medical data categories of the two nodes. For example, edge 412a can represent that a user enters a first expression of a patient's age, followed by a second expression of the patient's menopausal stage, into user interface 220, whereas edge 412b can represent that the user enters the second expression followed by the first expression.

Each directional edge between two nodes can be associated with a weight indicative of a probability for the next transition. For example, as shown in FIG. 4A, edge 412a can be associated with a weight 0.9, whereas edge 412b can be associated with a weight 0.1. Also, edge 414a can be associated with a weight 0.8, whereas edge 414b can be associated with a weight 0.1. Moreover, edge 416a can be associated with a weight 0.6, whereas edge 416b can be associated with a weight 0.1. Further, edge 418a can be associated with a weight 0.3, whereas edge 418b can be associated with a weight 0.05. A larger weight for a particular prior transition can indicate that such transition is more likely to occur when a user enters new medical data into user interface 220. In FIG. 4A, from node 402 (age), the most likely transition can be to node 404 (menopausal stage) as the weight for edge 412a (0.9) is the highest among all the edges going out of node 402, followed by node 406 (type of breast cancer), node 408 (breast cancer stage), and node 410 (treatment).

The weight of a directional edge from a first node to a second node can be determined based on a count of prior transitions from the first node to the second node according to the direction indicated by the directional edge. The weight can be determined based on, for example, dividing the count of prior transitions from the first node to the second node by a total count of prior transitions from the first node (to the second node and to other nodes). The directional edges can reflect a sequence of entry of medical data represented by the nodes. The prior transitions can be determined from prior entry of medical data by a particular user, or by a group of users, into user interface 220. A larger weight can reflect that such transition is more frequently recorded in the prior entry of the medical data, which can also indicate that such transition is more likely to occur when a user enters new medical data into user interface 220. Based on the weights, as well as the medical data category of the medical data just entered into user interface 220, standardized expression determination module 202 can predict the medical data category of a next set of medical data the user likely to enter into user interface 220, and generate candidate machine-predicted text strings based on the prediction.

FIG. 4B illustrates example operations involving historical medical data category sequences 214 in the generation of replacement text strings. As shown in FIG. 4B, after receiving input text strings 310 ("Jane Doe is 64") and entering replacement text strings 320a ("Jane Doe is a 64-year-old woman") into user interface 220, standardized expression determination module 202 can refer to historical medical data category sequences 214 and determine that it is at node 402 (age), based on looking up the term "age" associated with the medical data category determined for text strings 320a in historical medical data category sequences 214. Based on the weights of all outgoing edges from node 402, standardized expression determination module 202 can determine that the most likely transition is to node 404 (menopausal stage), which indicates that user is most likely going to enter medical data related to menopausal stage next into user interface 220. Standardized expression determination module 202 can refer back to medical data category table 212 and determine that the range of medical data values for the medical data category "menopausal stage" can include menopausal, peri-menopausal, and post-menopausal. From the range of medical data values, standardized expression determination module 202 can generate a set of candidate machine-predicted text strings 430 containing those medical data values and directed to menopausal stage, and display candidate predicted text strings 430 in user interface 220 for selection by the user. The selection can also be recorded and used to update the weight of edge 412a.

In some examples, the user can also enter input text strings 442 (e.g., "meno"), which can trigger standardized expression determination module 202 to look for a matching keyword/phrase from medical data category table 212 and generate a set of candidate replacement text strings identical to candidate machine-predicted text strings 430 for selection.

E. Generation of Medical Record

In addition, structured medical data generation module 206 can also update medical records 216 for a patient based on the replacement text strings and/or prediction text strings generated for text field 224. FIG. 5 illustrates an example of medical records 216 for a patient. As shown in FIG. 5, structured medical data generation module 206 can store the text strings 502 entered into text field 224, which include replacement text strings and prediction text strings, as unstructured medical data for the patient. The unstructured medical data can be in the form of a doctor's note, which can be presented to other clinicians/medical staff members for reading. In addition, structured medical data generation module 206 can create pairings of the medical data categories and the data values and store the pairings in a data structure, such as a data table 504, of medical records 216. The structured medical data can be provided to other software applications, which can interpret and analyze the data values based on the associated medical data category.

III. Example Operations of Text-Entry Assist System

Figure 6A:
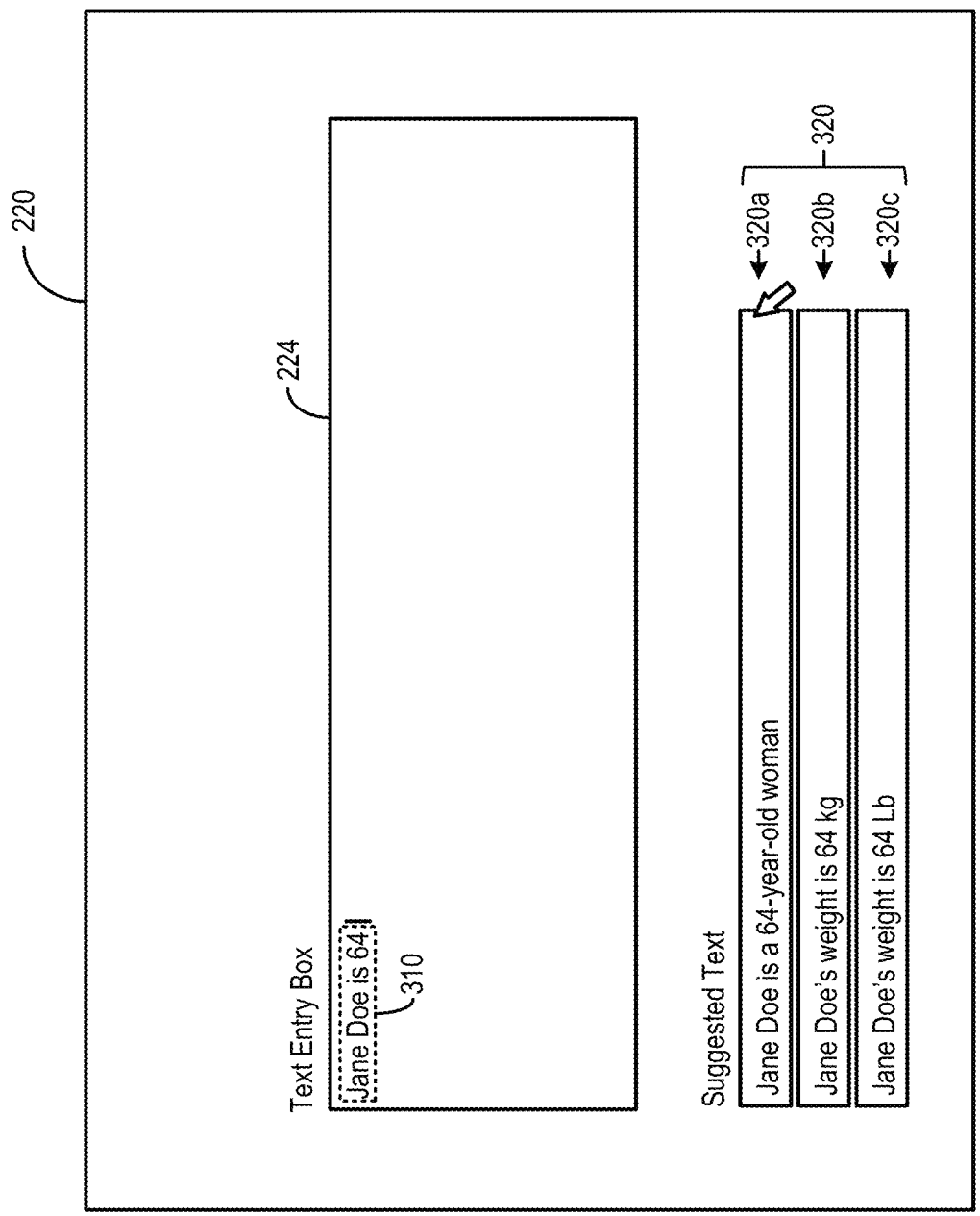
FIG. 6A, FIG. 6B, and FIG. 6C illustrate example display interfaces for interacting with text-entry assist system of FIG. 2, according to certain aspects of this disclosure.
Figure 6B:
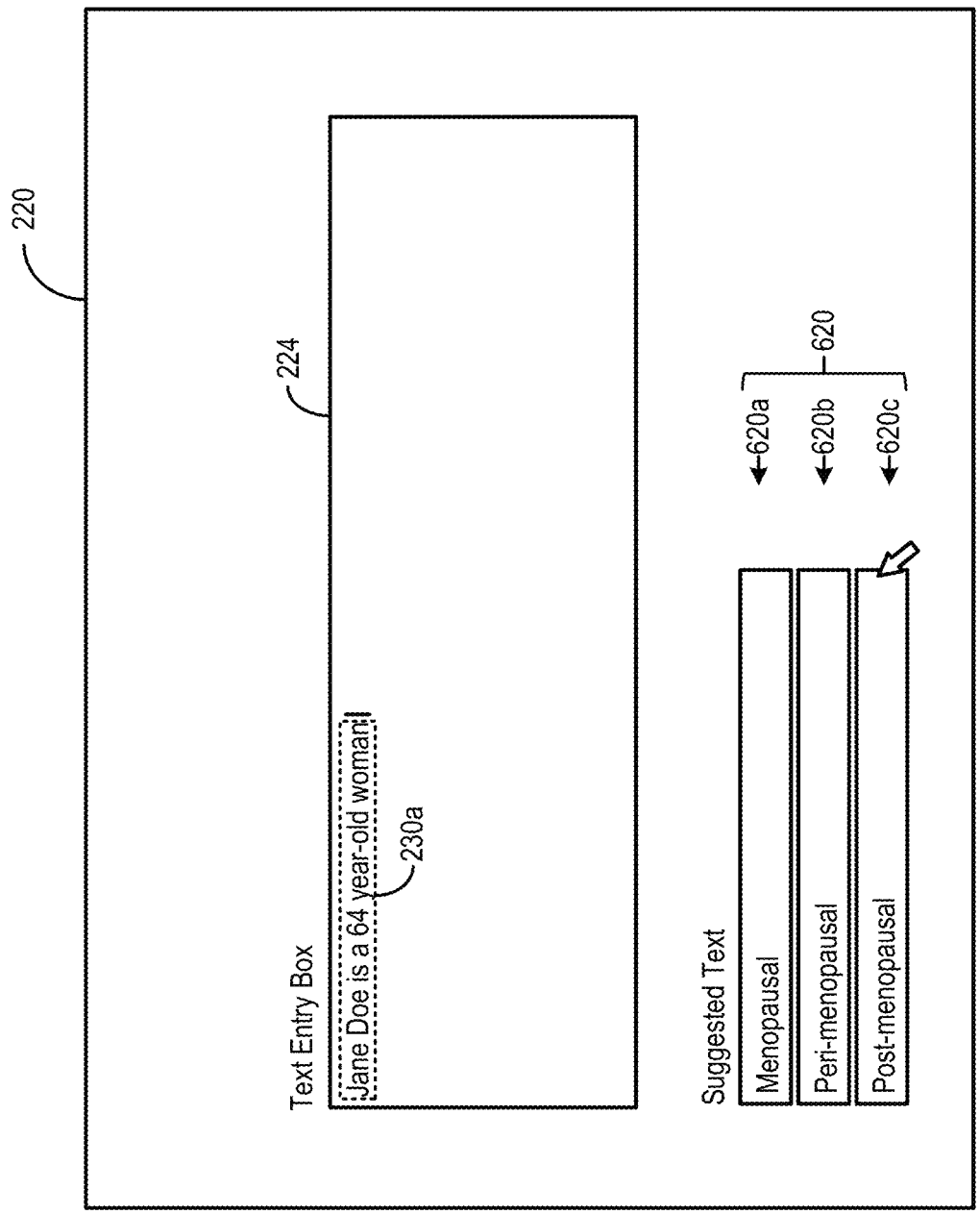
Figure 6C:
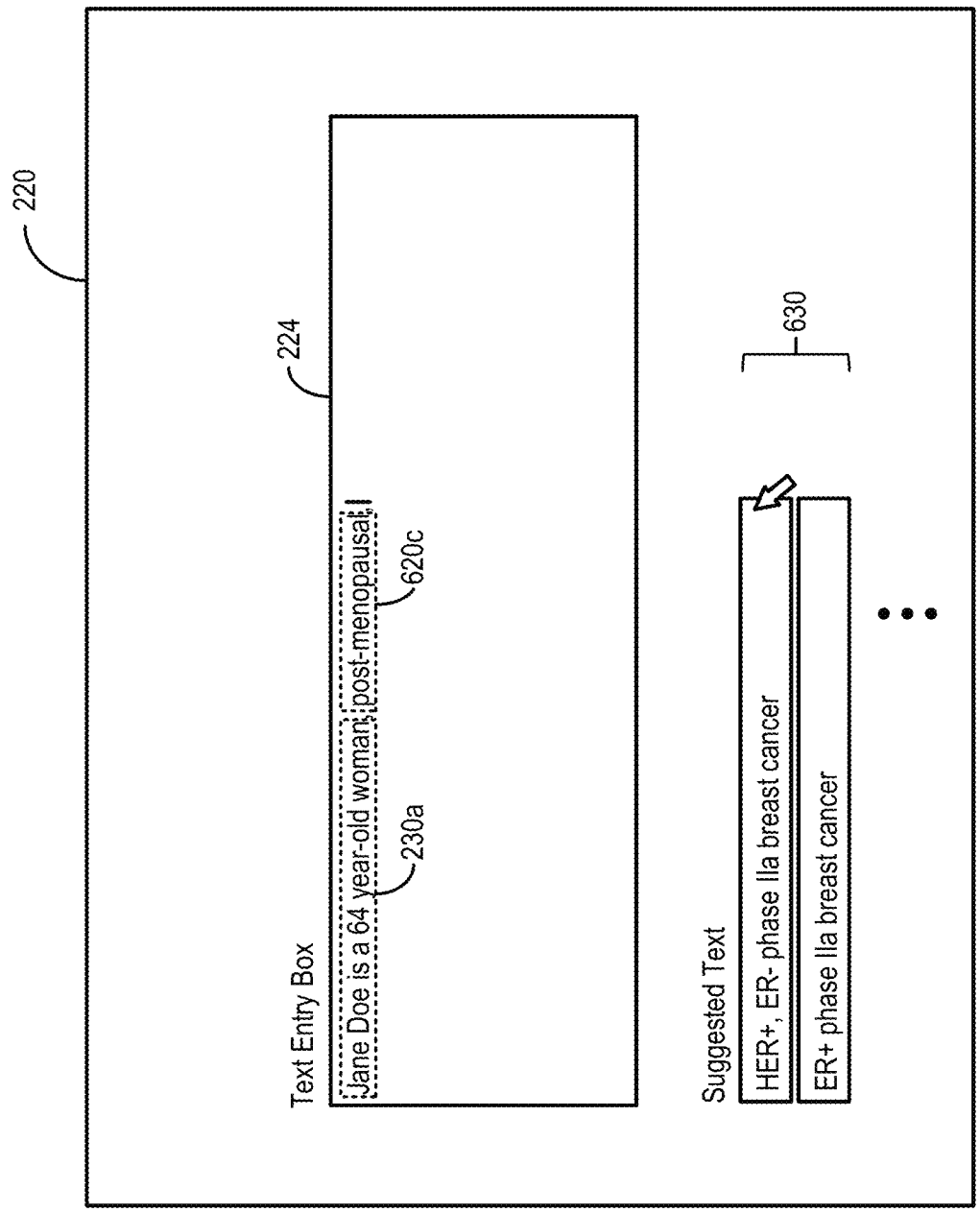

FIG. 6A, FIG. 6B, and FIG. 6C illustrate example operations of text-entry assist system 200 with user interface 220. As shown in FIG. 6A, standardized expression determination module 202 receives input text strings 310 ("Jane Doe is 64") in text field 224. Standardized expression determination module 202 can extract keyword "is" and data value "64" from input text strings 310. Standardized expression determination module 202 can determine a medical category within a pre-determined delay (e.g., 10 milliseconds) after it receives a first set of input text strings from which keywords are identified, and prior to receiving a subsequent set of input text strings from text field 224. Standardized expression determination module 202 can determine that the keyword matches with those associated with age, weight, and height in medical data category table 212, and display candidate replacement text strings 320 under the "suggested text strings" section of user interface 220. Each candidate replacement text is selectable.

Referring to FIG. 6B, upon detecting that the user selects the candidate replacement text 320a ("Jane Doe is a 64-year-old woman"), standardized expression determination module 220 can display replacement text 320a in text field 224 in place of input text strings 310. Before detecting additional input text strings from the user, standardized expression determination module 202 can refer to historical medical data sequences 214 and determine that, given that the most recently medical data category (age), the user is most likely to enter a next set of medical data for the menopausal stage of the patient. Standardized expression determination module 202 can refer to medical data category table 212 and generate a set of candidate prediction text strings 620 representing the range of data values for the menopausal stage of the patient, and provide the set of candidate prediction text strings for selection by the user under the "Suggested Text" section of user interface 220. In some examples, standardized expression determination module 202 can also generate and display candidate prediction text strings 620 based on detecting that the user enters new input text strings including the keywords for the menopausal stage (e.g., "meno").

Referring to FIG. 6C, upon detecting that the user selects the candidate prediction text string 620c ("post-menopausal"), standardized expression determination module 220 can add candidate prediction text string 620c to the back of replacement text strings 230a in text field 224. Standardized expression determination module 202 can add a pre-determined delimiter, such as a punctuation (e.g., a comma), between replacement text strings 230a and candidate prediction text string 620c based on the text strings belonging to different medical data categories. Before detecting additional input text strings from the user, standardized expression determination module 202 can refer to historical medical data sequences 214 and determine that, given that the most recently medical data category (menopausal stage), the user is most likely to enter a next set of medical data for the stage and type of breast cancer. Standardized expression determination module 202 can refer to medical data category table 212 and generate a set of candidate prediction text strings 630 representing different variations of stage and types of breast cancer, and provide the set of candidate prediction text strings for selection by the user under the "Suggested Text" section of user interface 220.

IV. Method

Figure 7:
FIG. 7 illustrates a method of assisting entry of text strings into a text field, according to certain aspects of this disclosure.

FIG. 7 illustrates a flowchart of a method 700 of assisting entry of text strings into a text field of a user interface (e.g., a website, a portal, etc.), as well as converting the unstructured text into structured text strings. The user interface can be part of a medical application that accepts text strings representing unstructured medical data input by a user (e.g., a clinician, a medical staff member, a data entry clerk, etc.), that stores the text strings, and that provides the medical data represented by the text strings for further processing, presentation, etc. Examples of the unstructured medical data can include, for example, pathological reports, doctor's notes, etc. The techniques can be implemented by a text-entry assist system that can be part of the user interface, or can be external to the user interface. Method 700 can be performed by, for example, text-entry assist system 200.

Method 700 starts with step 702, in which standardized expression determination module 202 receives, from text field 224 of user interface 220, one or more input text strings containing information of a patient from a user. The input text strings may include numerical values and phrases related to or indicative of a set of medical data of a patient. Each entry of the medical data can include a medical data category as well as one or more data values. For example, the medical data may include an age, a weight, a diagnosis result, treatment history, etc. The input text strings may include incomplete or a non-standardized expression of the patient's information.

In step 704, standardized expression determination module 202 identifies, based on language semantics and grammatical structure, a keyword and one or more data values from the input text strings. For example, referring back to the example of FIG. 3B, standardized expression determination module 202 can determine, based on English semantics and grammatical structure, that the input text strings include a subject, a verb, and a noun, and divide the text strings 310 into portions corresponding to a subject, a verb, and a noun. Standardized expression determination module 202 may determine that a noun including a numerical value is likely to include a medical data value for the patient. Standardized expression determination module 202 can then determine that the verb included in the input text strings is likely to include a keyword for a medical data category.

In step 706, standardized expression determination module 202 provides the keyword as an input to a query of a medical data category database, wherein the medical data category database stores a plurality of categories, each entry in the medical data category database including one of the plurality of categories in a first field and one or more keywords in a second field.

An example of medical data category database is shown as medical data category table 212 in FIG. 3A. Medical data category table 212 may store a plurality of medical data categories 302 such as age, weight, height, menopause stage, breast cancer stage, type of breast cancer, treatments, etc. Medical data category table 212 may also store keywords 304, with each medical data category being associated with one or more keywords. The keywords can be used by standardized expression determination module 202 to identify a medical data category included in input text strings received from the user via user interface 220. For example, as shown in FIG. 3A, the medical data category "age" can be associated with a set of keywords such as "age", "years of age", "age is", "is", etc. If the input text strings include at least one of those keywords, standardized expression determination module 202 can determine that the input text strings include the medical category "age". The keywords in medical data category table 212, as well as their association with the medical data categories, can be provided off-line by the user, by a manager of text-entry assist system 200 (e.g., based on analyzing the keywords used by a group of users to represent a medical data category), or based on an on-line learning process by learning module 208 as to be described below. In some examples, keywords 304 can include expressions/phrases in an non-English language (e.g., German, Spanish, etc.), which can be mapped to medical categories 302 and range of data values 306 represented in English. In addition, medical data category table 212 may also store ranges of data values 306, with each medical data category being associated with a range of data values.

In step 708, standardized expression determination module 202 receives, from the medical data category database, one or more categories associated with keyword, the one or more categories including a first category. One or more categories can be determined based on comparing the keyword identified from the input text strings and the keywords associated with the one or more categories in medical data category table 212. The comparison can be based on, for example, a degree of similarity (e.g., based on cosine distance, Euclidean distance, etc.) between the keyword identified in the input text strings and the one or more keywords associated with each medical data category in the medical data category table. In some examples, a plurality of medical data categories can be identified and ranked based on, for example, a likelihood of each medical data category being correctly associated with the one or more data values, prior selection by the user to associate a particular medical data category, etc., and the top ranked medical data category can be selected for the input text strings as the first category.

In step 710, standardized expression determination module 202 retrieves, from a template database, a first template associated with the first category, the first template including one or more fixed blocks and one or more variable blocks. An example of the first template is illustrated in FIG. 3B. The templates in the template database can be associated with the medical data categories in the medical data category database (e.g., medical data category table 212), and the first template can be retrieved based on the association with the first category.

In step 712, standardized expression determination module 202 inserts a data value corresponding to the keyword into a variable block of the first template to generate a replacement text string. For example, referring to FIG. 3B, standardized expression determination module 202 can insert a data value of the one or more data values of the input text strings (e.g., a number representing an age) into a variable block of the first template. The replacement text string is then displayed in place of the input text strings in the text field of the user interface, in step 714.

In some examples, standardized expression determination module 202 can generate a set of candidate replacement text strings based on a set of pre-determined templates. The templates can be identified for the first category, or a plurality of categories. The candidate replacement text strings can be ranked and displayed in the user interface for selection by the user. The selected candidate replacement text strings can then replace the input text strings.

In some examples, standardized expression determination module 202 can also predict a next set of medical data the user is likely to enter into the text field. The system can generate an expression representing the predicted medical data, and enter the expression into the text field on behalf of the user. The prediction can be based on, for example, prior sequences of medical data entered into the text field by the user or by a group of users. A sequence of medical data can include a sequence of medical data categories of the medical data category table.

In some examples, the prior sequences of medical data can be in the form of a graph including a set of nodes connected by directional edges. Each node can represent a medical data category included in, for example, medical data category table 212. Each node in the graph can be connected to another node via a pair of directional edges. Each pair directional edges can represent transitions between one medical data category to another medical category. A transition from one node to another node can indicate a sequential relationship between the medical data categories of the two nodes. Each directional edge between two nodes can be associated with a weight indicative of a probability for the next transition. A larger weight for a particular prior transition can indicate that such transition is more likely to occur when a user enters new medical data into user interface 220. The weight of a directional edge from a first node to a second node can be determined based on a count of prior transitions from the first node to the second node according to the direction indicated by the directional edge. The directional edges can reflect a sequence of entry of medical data represented by the nodes. The prior transitions can be determined from prior entry of medical data by a particular user, or by a group of users, into the user interface. A larger weight can reflect that such transition is more frequently recorded in the prior entry of the medical data, which can also indicate that such transition is more likely to occur when a user enters new medical data into user interface.

Based on identifying a medical data category for the input text strings, standardized expression determination module 202 can look up the node representing the identified medical data category from the graph, and identify one or more nodes that represent the subsequent medical categories likely to be entered by the user. The system can generate one or more candidate expressions representing the predicted medical data categories and display the expressions for selection. Upon receiving the selection, the system can then enter the selected candidate expression into the text field on behalf of the user.

V. Computer System

Figure 8:
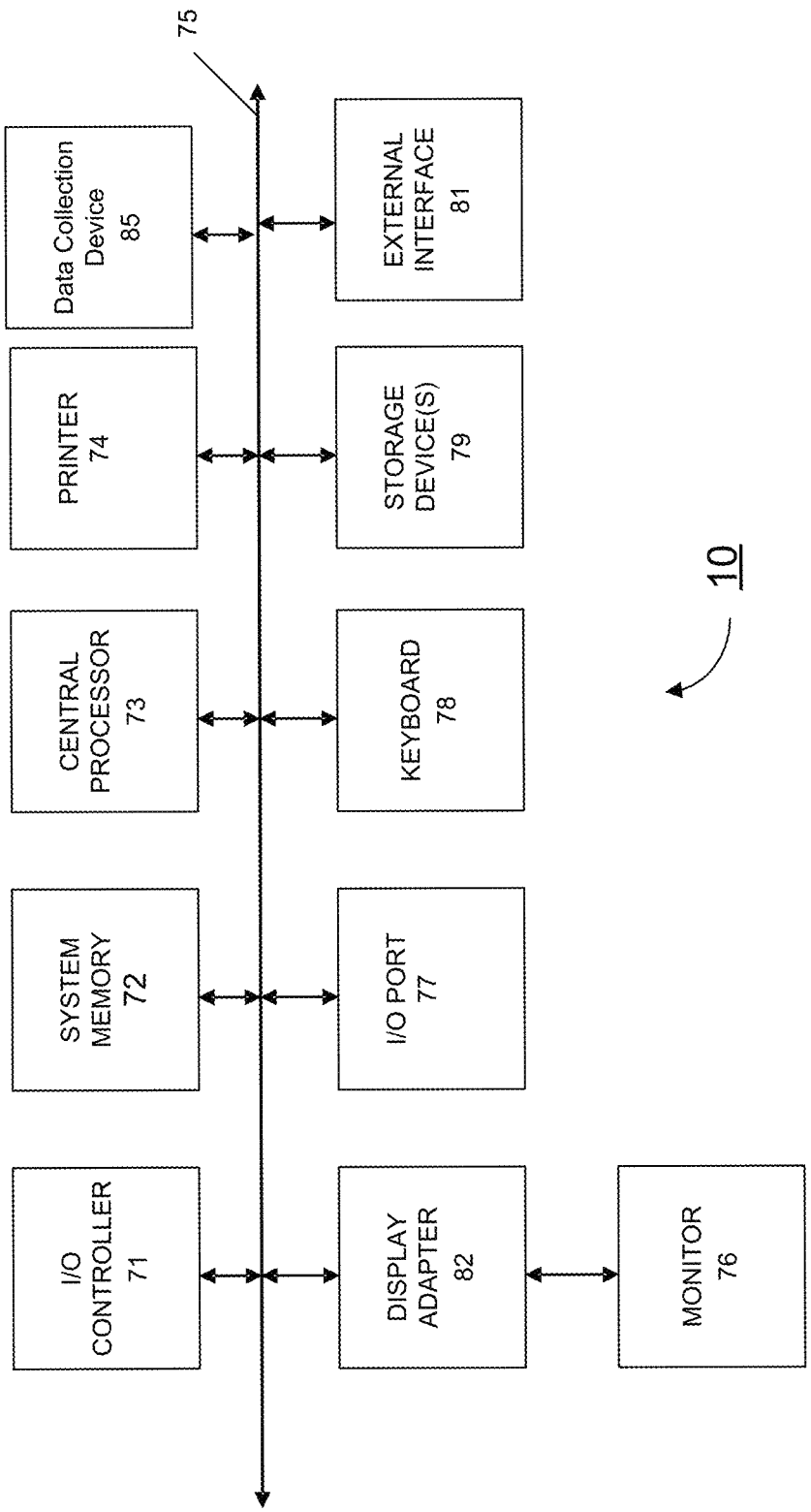
FIG. 8 illustrates an example computer system that may be utilized to implement techniques disclosed herein.

Any of the computer systems mentioned herein may utilize any suitable number of subsystems. Examples of such subsystems are shown in FIG. 8 in the computer system 10. In some examples, a computer system includes a single computer apparatus, where the subsystems can be the components of the computer apparatus. In other examples, a computer system can include multiple computer apparatuses, each being a subsystem, with internal components. A computer system can include desktop and laptop computers, tablets, mobile phones and other mobile devices. In some examples, a cloud infrastructure (e.g., Amazon Web Services), a graphical processing unit (GPU), etc., can be used to implement the disclosed techniques.

The subsystems shown in FIG. 8 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect the computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some examples, computer systems, subsystem, or apparatuses can communicate over a network. In such instances, one computer can be considered a client and another computer a server, where each can be part of a same computer system. A client and a server can each include multiple systems, subsystems, or components.

Aspects of examples can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement examples of the present disclosure using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, examples can be directed to computer systems configured to perform the steps of any of the methods described herein, potentially with different components performing a respective step or a respective group of steps. Although presented as numbered steps, steps of methods herein can be performed at the same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular examples may be combined in any suitable manner without departing from the spirit and scope of this disclosure. However, other examples of the present disclosure may be directed to specific examples relating to each individual aspect, or specific combinations of these individual aspects.

The above description of examples of the present disclosure has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A computer-implemented method, comprising:
receiving, from a text field of a user interface, input text strings containing medical data;
identifying, based on language semantics and grammatical structure, a keyword and one or more medical data values from the input text strings;
providing the keyword as an input to a query of a medical data category database, wherein the medical data category database stores a plurality of medical data categories, each entry in the medical data category database including one of the plurality of medical data categories in a first field and one or more keywords in a second field;
receiving, from the medical data category database, one or more medical data categories associated with the keyword, the one or more medical data categories including a first medical data category;
determining, from the medical data category database, a set of candidate replacement text strings, wherein the set of candidate replacement text strings are determined based on keywords associated with the set of candidate replacement text strings matching the identified keyword, wherein determining the set of candidate replacement text strings comprises:
retrieving, from a template database, a first template associated with the first medical data category, the first template including one or more fixed blocks comprising pre-determined text strings of an expression for the first medical data category and one or more variable blocks for a medical data value of the one or more medical data values that is a value for the first medical data category;
inserting the medical data value of the one or more medical data values from the input text strings corresponding to the keyword into a variable block of the first template to generate one or more replacement text strings of the set of candidate replacement text strings representing (a) the expression for the first medical data category and (b) the medical data value;
receiving a user selection of the one or more replacement text strings of the set of candidate replacement text strings; and
displaying the one or more replacement text strings in place of the input text strings in the text field.

2. The method of claim 1, further comprising:
displaying the set of candidate replacement text strings in the user interface,
wherein the user selection of one of the set of candidate replacement text strings is received in the user interface; and
determining the selected one of the set of candidate replacement text strings as the replacement text strings.

3. The method of claim 1, wherein the keywords associated with the set of candidate replacement text strings include non-English text strings; and
wherein the set of candidate replacement text strings are in English.

4. The method of claim 1, wherein the set of candidate replacement text strings are determined based on a degree of similarity between the keywords associated with the set of candidate replacement text strings and the identified keyword exceeding a pre-determined threshold.

5. The method of claim 4, wherein the set of candidate replacement text strings comprise a plurality of candidate replacement text strings; and
wherein the method further comprises:
ranking the plurality of candidate replacement text strings; and
displaying the plurality of candidate replacement text strings in the user interface based on the ranking.

6. The method of claim 5, wherein the ranking is based on the one or more medical data values.

7. The method of claim 6, wherein each of the plurality of candidate replacement text strings is associated with a medical data category in the medical data category database;
wherein each medical data category is associated with a probability distribution of data values; and
wherein the ranking is determined based on a likelihood of the medical data category associated with the respective set of candidate replacement text strings being correctly associated with the one or more medical data values, the likelihood being determined based on the probability distribution of the medical data category associated with the respective set of candidate replacement text strings.

8. The method of claim 6, wherein the ranking is based on a history of selection of the candidate replacement text strings by a user.

9. The method of claim 1, wherein the input text strings are first input text strings;
wherein the keyword is first keyword;
wherein the method further comprises:
receiving, from the text field, second input text strings;
extracting, from the second input text strings, a second keyword;
determining that the second keyword is not in the medical data category database; and
responsive to determining that the second keyword is not in the medical data category database, adding the second keyword to the medical data category database.

10. The method of claim 9, further comprising: removing the second input text strings from being displayed in the text field.

11. The method of claim 1, wherein the method further comprises:
determining, from historical medical data sequences, and the first medical data category, a second category of medical data a user is likely to enter into the text field after the input text strings;
determining prediction text strings representing the second category; and
displaying the prediction text strings with the replacement text strings in the text field.

12. The method of claim 11, wherein the historical medical data sequences comprises a graph comprising a plurality of nodes connected by directional edges;
wherein each node represents a category of the plurality of medical data categories stored in the medical data category database;
wherein a pair of nodes are connected by a pair of directional edges, each directional edge within the pair being associated with a weight indicative of a likelihood of one node of the pair transitioning to another node of the pair; and
wherein a next set of medical data is determined based on:
determining a first node of the plurality of nodes corresponding to the first medical data category;
identifying a second node based on weights of outgoing directional edges from the first node; and
determining the second category represented by the second node.

13. The method of claim 1, further comprising:
storing the replacement text strings as unstructured medical data of a medical record of a patient.

14. The method of claim 1, further comprising:
creating a pairing between the first medical data category and the one or more medical data values; and
storing the pairing in a medical data database as structured medical data of a medical record of a patient.

15. The method of claim 1, wherein the keyword and the input text strings are identified based on a natural language processor (NLP) model.

16. An apparatus comprising:
a memory that stores a set of instructions; and
a hardware processor configured to execute the set of instructions to:
receive, from a text field of a user interface, input text strings containing medical data;

identify, based on language semantics and grammatical structure, a keyword and one or more medical data values from the input text strings;

provide the keyword as an input to a query of a medical data category database, wherein the medical data category database stores a plurality of medical data categories, each entry in the medical data category database including one of the plurality of medical data categories in a first field and one or more keywords in a second field;

receive, from the medical data category database, one or more medical data categories associated with the keyword, the one or more medical data categories including a first medical data category;

determine, from the medical data category database, a set of candidate replacement text strings, wherein the set of candidate replacement text strings are determined based on keywords associated with the set of candidate replacement text strings matching the identified keyword, wherein determining the set of candidate replacement text strings comprises:

retrieving, from a template database, a first template associated with the first medical data category, the first template including one or more fixed blocks comprising pre-determined text strings of an expression for the first medical data category and one or more variable blocks for a medical data value of the one or more medical data values that is a value for the first medical data category; and inserting the medical data value of the one or more medical data values from the input text strings corresponding to the keyword into a variable block of the first template to generate one or more replacement text strings of the set of candidate replacement text strings representing (a) the expression for the first medical data category and (b) the medical data value;

receive a user selection of the one or more replacement text strings of the set of candidate replacement text strings; and provide the one or more replacement text strings to the user interface to be displayed in place of the input text strings in the text field.

17. The apparatus of claim 16, wherein the hardware processor is further configured to:

determine, from historical medical data sequences, and the first medical data category, a second category of medical data a user is likely to enter into the text field after the input text strings;

determine prediction text strings representing the second category; and provide the prediction text strings to the user interface to be displayed with the replacement text strings in the text field.

18. A non-transitory computer readable medium storing instructions that, when executed by a hardware processor, causes the hardware processor to:

receive, from a text field of a user interface, input text strings containing medical data;

identify, based on language semantics and grammatical structure, a keyword and one or more medical data values from the input text strings;

provide the keyword as an input to a query of a medical data category database, wherein the medical data category database stores a plurality of medical data categories, each entry in the medical data category database including one of the plurality of medical data categories in a first field and one or more keywords in a second field;

receive, from the medical data category database, one or more medical data categories associated with the keyword, the one or more medical data categories including a first medical data category;

determine, from the medical data category database, a set of candidate replacement text strings, wherein the set of candidate replacement text strings are determined based on keywords associated with the set of candidate replacement text strings matching the identified keyword, wherein determining the set of candidate replacement text strings comprises:

retrieving, from a template database, a first template associated with the first medical data category, the first template including one or more fixed blocks comprising pre-determined text strings of an expression for the first medical data category and one or more variable blocks for a medical data value of the one or more medical data values that is a value for the first medical data category; and inserting the medical data value of the one or more medical data values from the input text strings corresponding to the keyword into a variable block of the first template to generate one or more replacement text strings of the set of candidate replacement text strings representing (a) the expression for the first medical data category and (b) the medical data value;

receive a user selection of the one or more replacement text strings of the set of candidate replacement text strings; and provide the one or more replacement text strings to the user interface to be displayed in place of the input text strings in the text field.

19. The non-transitory computer readable medium of claim 18, further comprising instructions that, when executed by the hardware processor, causes the hardware processor to:

determine, from historical medical data sequences and the first medical data category, a second medical data category of medical data a user is likely to enter into the text field after the input text strings;

determine prediction text strings representing the second medical data category; and provide the prediction text strings to the user interface to be displayed with the replacement text strings in the text field.

* * * * *